(12) United States Patent
Sirpad et al.

(10) Patent No.: US 9,545,233 B2
(45) Date of Patent: Jan. 17, 2017

(54) ON-SITE VERIFICATION OF IMPLANT POSITIONING

(71) Applicant: Mazor Robotics Ltd., Caesarea (IL)

(72) Inventors: Yael Sirpad, Meitar (IL); Eli Zehavi, Haifa (IL); Moshe Shoham, Hoshaya (IL); Leonid Kleyman, Acco (IL)

(73) Assignee: MAZOR ROBOTICS LTD., Caesaria (IL)

( * ) Notice: Subject to any disclaimer, the term of this patent is extended or adjusted under 35 U.S.C. 154(b) by 0 days.

(21) Appl. No.: 14/402,696

(22) PCT Filed: May 21, 2013

(86) PCT No.: PCT/IL2013/050437
§ 371 (c)(1),
(2) Date: Nov. 21, 2014

(87) PCT Pub. No.: WO2013/175471
PCT Pub. Date: Nov. 28, 2013

(65) Prior Publication Data
US 2015/0150523 A1     Jun. 4, 2015

Related U.S. Application Data

(60) Provisional application No. 61/650,242, filed on May 22, 2012.

(51) Int. Cl.
*G06K 9/00*     (2006.01)
*A61B 6/12*     (2006.01)
(Continued)

(52) U.S. Cl.
CPC ............. *A61B 6/12* (2013.01); *A61B 6/5235* (2013.01); *A61B 6/5247* (2013.01); *A61B 90/36* (2016.02);
(Continued)

(58) Field of Classification Search
CPC ... A61B 6/12; A61B 19/52; A61B 2019/5289; A61B 2019/5295; A61B 2019/5238; A61B 2019/5466; A61B 6/5247; A61B 6/5235; G06T 2207/30008; G06T 15/00; G06T 7/004; G06T 2207/10121; G06K 9/6202
(Continued)

(56) References Cited

U.S. PATENT DOCUMENTS 5,963,612 A    10/1999  Navab
6,049,582 A     4/2000  Navab
(Continued)

FOREIGN PATENT DOCUMENTS

WO    WO0064367 A1   11/2000
WO    WO0237935 A2    5/2002
(Continued)

OTHER PUBLICATIONS

Extended European Supplementary Search Report of EP13793369.3, dated Mar. 2, 2016.
(Continued)

*Primary Examiner* — Gregory F Cunningham
(74) *Attorney, Agent, or Firm* — Daniel Feigelson; Fourth Dimension IP

(57) ABSTRACT

A method verifying the position of a surgically inserted orthopedic insert. A preoperative three dimensional image data set of the surgical site is generated, showing the bone into which the insert is to be inserted. During the insertion procedure, a series of intraoperative two-dimensional fluoroscope images are generated, each at a known pose relative to the bone, showing the insert during or after insertion into the bone. The 3-D position of the insert is determined in an intraoperative three dimensional image data set reconstructed from the series of intraoperative 2-D fluoroscope
(Continued)

images. The reconstructed intraoperative 3-D image data set is registered with the preoperative three dimensional image data set, such as by comparison of imaged anatomical features. Once this registration is achieved, the determined 3-D position of the insert is used to implant a virtual image of the insert into the preoperative three dimensional image data set.

14 Claims, 3 Drawing Sheets

(51) Int. Cl.
  *A61B 6/00* (2006.01)
  *G06K 9/62* (2006.01)
  *G06T 7/00* (2006.01)
  *G06T 15/00* (2011.01)
(52) U.S. Cl.
  CPC ............ *G06K 9/6202* (2013.01); *G06T 7/004* (2013.01); *G06T 15/00* (2013.01); *A61B 2090/364* (2016.02); *A61B 2090/367* (2016.02); *A61B 2090/376* (2016.02); *A61B 2090/3966* (2016.02); *G06T 2207/10121* (2013.01); *G06T 2207/30008* (2013.01)
(58) Field of Classification Search
  USPC ........................................................ 382/132
  See application file for complete search history.

(56) References Cited

U.S. PATENT DOCUMENTS

| | | | |
|---|---|---|---|
| 6,069,932 A | 5/2000 | Peshkin et al. | |
| 6,118,845 A | 9/2000 | Simon et al. | |
| 6,206,566 B1 | 3/2001 | Schuetz | |
| 6,359,960 B1 | 3/2002 | Wahl et al. | |
| 6,370,224 B1 | 4/2002 | Simon et al. | |
| 6,379,041 B1 | 4/2002 | Schuetz et al. | |
| 6,666,579 B2 | 12/2003 | Jensen | |
| 6,711,432 B1 | 3/2004 | Krause et al. | |
| 6,851,855 B2 | 2/2005 | Mitschke et al. | |
| 7,142,633 B2 | 11/2006 | Eberhard et al. | |
| 7,689,014 B2 | 3/2010 | Abovitz et al. | |
| 7,804,991 B2 | 9/2010 | Abovitz et al. | |
| 8,218,843 B2 | 7/2012 | Edlauer et al. | |
| 8,233,690 B2 | 7/2012 | Ng et al. | |
| 2003/0074011 A1* | 4/2003 | Gilboa | A61B 5/06 606/130 |
| 2004/0043368 A1* | 3/2004 | Hsieh | G09B 23/28 434/262 |
| 2004/0044295 A1* | 3/2004 | Reinert | A61B 17/1757 600/587 |
| 2006/0262970 A1* | 11/2006 | Boese | G03B 42/023 382/131 |
| 2008/0269596 A1* | 10/2008 | Revie | A61B 6/12 600/424 |
| 2008/0306490 A1* | 12/2008 | Lakin | A61B 5/064 606/130 |
| 2010/0030232 A1* | 2/2010 | Zehavi et al. | 606/130 |
| 2010/0069913 A1* | 3/2010 | Chirico et al. | 606/94 |
| 2010/0284601 A1* | 11/2010 | Rubner et al. | 382/132 |
| 2011/0268325 A1 | 11/2011 | Teichman et al. | |
| 2014/0064583 A1 | 3/2014 | Wang et al. | |
| 2014/0275985 A1* | 9/2014 | Walker et al. | 600/424 |
| 2015/0029185 A1 | 1/2015 | Ikits | |

FOREIGN PATENT DOCUMENTS

| | | |
|---|---|---|
| WO | WO2005087125 A2 | 9/2005 |
| WO | WO2007009263 A1 | 1/2007 |
| WO | WO2008038283 A2 | 4/2008 |
| WO | WO2011136988 A1 | 11/2011 |

OTHER PUBLICATIONS

International Search Report for PCT/IL2013/050437 published as WO/2013/175471.
Written Opinion for PCT/IL2013/050437 published as WO/2013/175471.

* cited by examiner

ON-SITE VERIFICATION OF IMPLANT POSITIONING

This is a 35 U.S.C. §371 application of PCT/IL2013/050437, filed May 21, 2013, and claims the benefit under 35 U.S.C. §120 of said PCT application, and further claims the benefit under 35 U.S.C. §119(e) of U.S. Provisional Patent Application USSN 61/650242, filed May 22, 2012. The contents of these priority applications are incorporated herein by reference.

FIELD OF THE INVENTION

The present invention relates to the field of intraoperative fluoroscopic imaging of orthopedic implants, and especially for use in verifying the spatial accuracy of the position of the implant during the course of the operation.

BACKGROUND OF THE INVENTION

In orthopedic surgery, intraoperative fluoroscopic images are extensively used in order to ascertain the alignment of orthopedic implants, such that they are inserted into their predetermined positions, as selected by the surgeon generally using preoperative three-dimensional images, such as CT images. Such intra-operative fluoroscopic images are also used in order to ascertain that the orthopedic implants have been inserted into their correct position at the conclusion of the operation. However, such verification may be difficult to perform since although the implants, generally being metallic, show up with high contrast in the intra-operative x-ray images, the anatomical features around them may have much weaker contrast, and, because of the depth of soft tissue and bone through which the x-ray image is being taken, various image artifacts may make the X ray image difficult to interpret. Consequently, in the typically blurred fluoroscope image, it may be difficult to associate the position of the implant with the unclearly defined surrounding bone structure into which the insert has been placed. Currently this is a problematic situation, since the verification of an implant location can only be performed after closing the operating site, and sending the patient for a high definition 3-D imaging procedure, such as a CT or an MRI procedure, in which the soft tissues and bone are also clearly defined. If this procedure shows that the implant is not in the correct position, then the patient must undergo a correction operation, with its associated discomfort and costs.

This problem is particularly acute in spinal operations, such as those which use pedicle screws for spinal fusion for instance, the accuracy of the placement of the screws being highly critical because of the proximity of sensitive neurological features. Because of the complex orthopedic structural nature of the vertebrae themselves and of their associated muscles and ligaments, determination of the spatial position and angle of a pedicle screw is difficult to define in a two-dimensional x-ray image.

There therefore exists a need for an imaging technique which enables the verification of the accurate 3D positioning of an insert during the operation itself, such that it overcomes at least some of the disadvantages of prior art methods.

The disclosures of each of the publications mentioned in this section and in other sections of the specification, are hereby incorporated by reference, each in its entirety.

SUMMARY

The present disclosure describes new exemplary systems and methods for providing intraoperative verification of the position of an orthopedic insert, by implanting a virtual image of the true three dimensional position of the insert as determined from a series of intraoperative two dimensional fluoroscope images, on a preoperatively generated three dimensional image set of the surgical site.

There exist a number of systems especially for use in orthopedic surgery, in which intra-operatively generated two-dimensional images, such as X-ray fluoroscope images, are correlated to preoperatively generated three-dimensional images, such as CT images. One such system is that described in the International Patent Application published as WO 2008038283 for "C-arm Computerized Tomography System, assigned to Mazor Robotics Ltd., hereby incorporated by reference in its entirety. In that application, three dimensional CT-type information is generated from a conventional C-arm fluoroscope imaging system which provides two-dimensional images. This enables the adaptation of widely used C-arm installations to provide CT-type information.

That system uses a three dimensional target containing radiographically opaque markers having predetermined mutual positions, such that an image of the target can be analyzed to determine the position and orientation of the target relative to the C-arm. The target is disposed in a fixed position relative to the subject, and a sequence of at least two images, or a video segment is obtained of a region of interest of a subject while the C-arm is moved around the subject, either manually or, for those systems where provided, by a motor. No assumptions are made regarding the centricity of the C-arm or the relative position of the patient, as long as the region of interest appears in the sequence of images, or at least in the majority of the frames of such a video sequence.

Each of the images is analyzed by the system software to determine the pose of the C-arm relative to the subject by analysis of the image patterns of the target. Images are then selected, according to various criteria, to provide the imaged data of the region of interest of the subject. Alternatively and preferably, at least a selected number of frames from the video sequence, or a number of fields in the case of interlaced video, are selected and analyzed to determine the pose of the C-arm relative to the subject by analysis of the image patterns of the target. According to either of these methods, a series of two-dimensional image data is obtained with associated positional data for each image, and this information is used to reconstruct a three dimensional volumetric set of imaging data of the region of interest of the subject. Though this series can be made up of data from only two two-dimensional images, the greater the number of image data sets acquired, the better is the quality of the reconstructed three dimensional volumetric set of imaging data.

The pose of the C-arm relative to the subject is determined by the use of a three dimensional target, incorporating a three dimensional array of X-ray opaque marker points, which should be visible on the fluoroscope images. The target is disposed in a position close to or on the subject, such that at least a part of the image of the target is seen in the fluoroscope images. The target must be affixed, either to the subject or to the operating table or bed on which the subject is fixed, so that its position is unchanged relative to the subject. The target image information is processed using a conventional algorithm used for this purpose, to determine the angular and translational position of the C-arm at any point in time, such that the system software can thus determine the position and orientation of the anatomical part of the subject within the imaged data of each frame. The target is preferably tracked along the video sequence using a dynamic model in order to increase accuracy, speed, and robustness of the pose estimation.

Although the imaging of a three-dimensional target provides a convenient and "built-in" method of determining the pose of each of the intraoperative C-arm images, it is to be understood that this is only one method of providing this information, and the methods of the present disclosure can be implemented using any other method which provides three-dimensional image orientation information for each image generated, such as angular position sensors on the C-arm, or an external optical navigation system, or the like.

The output data from the sequence of video frames grabbed by the system software is processed by means of a reconstruction engine to generate CT-type data, enabling three-dimensional images of the region of interest to be constructed. This generated image could be called an "intraoperative virtual CT" image, since it is synthesized from intraoperative two-dimensional fluoroscope images, each image being associated with a known imaging orientation and position. However once the reconstruction has been completed, it is possible to extract from this virtual CT data, any plane which the surgeon may wish to view, whether AP, AX or LT. It differs in one important feature from the preoperative CT data in that the real implant now also appears as a three dimensional feature in the images, along with the rest of the anatomical features of the operation site. The three-dimensional image of the insert, because of its high contrast level, can be visualized clearly in the intraoperative virtual CT.

However whereas the preoperative CT images should show all of the anatomical features clearly delineated, the intraoperative virtual CT may not show all of these anatomical features clearly, because of the above-mentioned problems associated with the fluoroscopic imaging of a complex operating site with complex and thick layers of soft tissue together with the bone and the insert. More importantly, whenever a comparatively large radiographically opaque object is imaged ("comparatively large" meaning of size comparable with the size of the details to be discerned), artifacts are generated because the high contrast implant "shadows" the image details. However the reconstruction process, by using data from multiple images—even if only two images, but generally many more—enables a three dimensional data set of the operation site to be obtained containing more information than any one of the two-dimensional fluoroscopic images alone. Therefore the ability to discern anatomical features of the operation site in the intraoperative virtual CT should be improved over the situation existent with the individual fluoroscope images.

It thus becomes possible to perform a good registration between the intraoperatively generated virtual CT data, and the preoperatively generated CT data. Such a registration can be performed by any of the methods known in the art, such as comparison of anatomical features or intensity comparisons between corresponding planes of the two compared CT image sets. Once this registration has been performed, then according to the methods of the present disclosure, the position of the clearly defined image of the insert determined from the intraoperative virtual CT data, can be implanted into the corresponding planes of the preoperative CT data. By this means it becomes possible to artificially display the intraoperative position of the insert in the preoperative images, which were obviously obtained without the insert. The accurately known position of the insert can then be accurately defined on the high-quality images of the bones and surrounding tissues of the operation site, as determined from the preoperative CT image set. Using these images, the surgeon can then ascertain with a higher level of reliability and accuracy, the position of the insert in relation to the orthopedic structure in which it has been inserted. A decision can then be made intraoperatively whether the insert position is acceptable, without the need for obtaining a post-operative CT image of the operation site. This method is therefore obviously greatly advantageous over prior art methods of verification of the position of inserts only after the operation has been completed, and generally at a different site.

The method has been described above using a sequence of 2-dimensional fluoroscope images to reconstruct the 3-dimensional virtual CT image data. However, it is feasible that registration may be achievable from only two C-arm images, which might provide clinically acceptable three-dimensional data for some applications. However, such implementations are likely to be limited. In particular, they are unlikely to be useful for spinal procedures, since the best orientation for determining the accuracy of positioning of a pedicle screw is the axial plane. The full 3-dimensional reconstruction is preferably used for these cases since using X-ray fluoroscope images alone, it is impossible to obtain axial views of the vertebrae.

When applied to the verification of the positioning of a pedicle screw implant in the subject's spine, the system and method uses imagery from existing C-arms, which are standard equipment in spine operating rooms, as opposed to either waiting for a post operative CT scan, or using an additional, expensive intra-operative 3D system installed in the spine surgery operating room. A short, typically 15 second C-arm scan is performed after screw positioning, and the images obtained are fused, using the method described above, with high-quality images from the preoperative CT. This produces an intra-operative 3D axial view of the spine, showing the exact location of each pedicle screw and its relationship to the spinal canal. Consequently, if a repositioning of a screw is necessary, it can be done immediately, rather than as a revision case at a later time. The process requires no more than several minutes of additional OR time, and the patient receives the equivalent of a postoperative CT before leaving the operating room and at a substantially lower radiation exposure.

Furthermore, there are also other prior art systems which correlate two-dimensional fluoroscope images to preoperative CT images, such as those mentioned in the background section of the above referenced WO 2008/038283. The methods described in this disclosure, of performing registration of intraoperative X ray to preoperative CT images, are understood to be equally applicable to such systems too, and are not meant to be limited to the C-arm application.

Finally, although this disclosure has used CT images as the exemplary preoperatively generated three dimensional image set, it is to be understood that the application is not intended to be so limited, and that MRI imaging could be equally well used for that imaging mode.

One exemplary implementation described in this application involves a method of analyzing intraoperative images of a surgically inserted orthopedic insert, comprising:
(i) generating a preoperative three dimensional image data set showing at least a bone in which the insert is to be inserted,
(ii) generating a plurality of intraoperative two-dimensional fluoroscope images, each taken at a known orientation and position relative to the bone, showing the insert and the bone, (iii) determining the three dimensional position of the insert in at least one intraoperative three dimensional image data set reconstructed from the plurality of intraoperative two-dimensional fluoroscope images, (iv) registering the at least one intraoperative three dimensional image data set with the preoperative three dimensional image data set, and (v) using the determined three dimensional position of the insert to implant an image of the insert into the preoperative three dimensional image data set.

The above mentioned method may further comprise the steps of:

(vi) defining on the preoperative three dimensional image data set the planned position of the insert relative to the bone, and (vii) comparing the implanted image of the insert in the preoperative three dimensional image data set with the planned position of the insert relative to the bone.

In either of the above mentioned methods, the registering may be performed by comparing anatomical features determined from the at least one intraoperative three dimensional image data set with corresponding features on the preoperative three dimensional image data set. Alternatively, the registering may be performed by comparing intensity features determined from the at least one intraoperative three dimensional image data set with corresponding features on the preoperative three dimensional image data set.

In other implementations of such methods, the at least one bone may be a vertebra, and the insert may be a pedicle screw, an obliquely inserted screw or an artificial disc. Additionally, the preoperative three dimensional image data set may be either a CT data set or an MRI data set.

Additional implementations may involve a method as described above, wherein the plurality of intraoperative two-dimensional fluoroscope images taken at known orientations and positions may be obtained using a C-arm system.

Furthermore, according to any of these methods, the known orientations and positions of the plurality of intraoperative two-dimensional fluoroscope images may be determined by analyzing images of a three dimensional target disposed in a fixed position relative to the bone, and featured in the plurality of intraoperative two-dimensional fluoroscope images. In such a case, the three dimensional target may comprise radiographically opaque markers having predetermined mutual positions.

In other implementations of this method, the known orientations and positions of the plurality of intraoperative two-dimensional fluoroscope images may be determined by use of an optical system tracking the orientation and position of the system generating the fluoroscope images. Alternatively, the known orientations and positions of the plurality of intraoperative two-dimensional fluoroscope images may be determined by use of orientation sensors on the system generating the fluoroscope images.

In any of the above-described methods, the plurality of intraoperative two-dimensional fluoroscope images may be a video sequence of images.

Additionally, the intraoperative position and orientation of the insert, as determined in the plurality of intraoperative images, may be virtually displayed in the three dimensional image data set obtained preoperatively without the insert.

Finally, according to any of the above described methods, the plurality of intraoperative two-dimensional fluoroscope images, each taken at a known orientation and position relative to the bone, may show the insert during insertion into said bone or on completion of insertion into said bone.

BRIEF DESCRIPTION OF THE DRAWINGS

The presently claimed invention will be understood and appreciated more fully from the following detailed description, taken in conjunction with the drawings in which:

DETAILED DESCRIPTION

Figure 1:
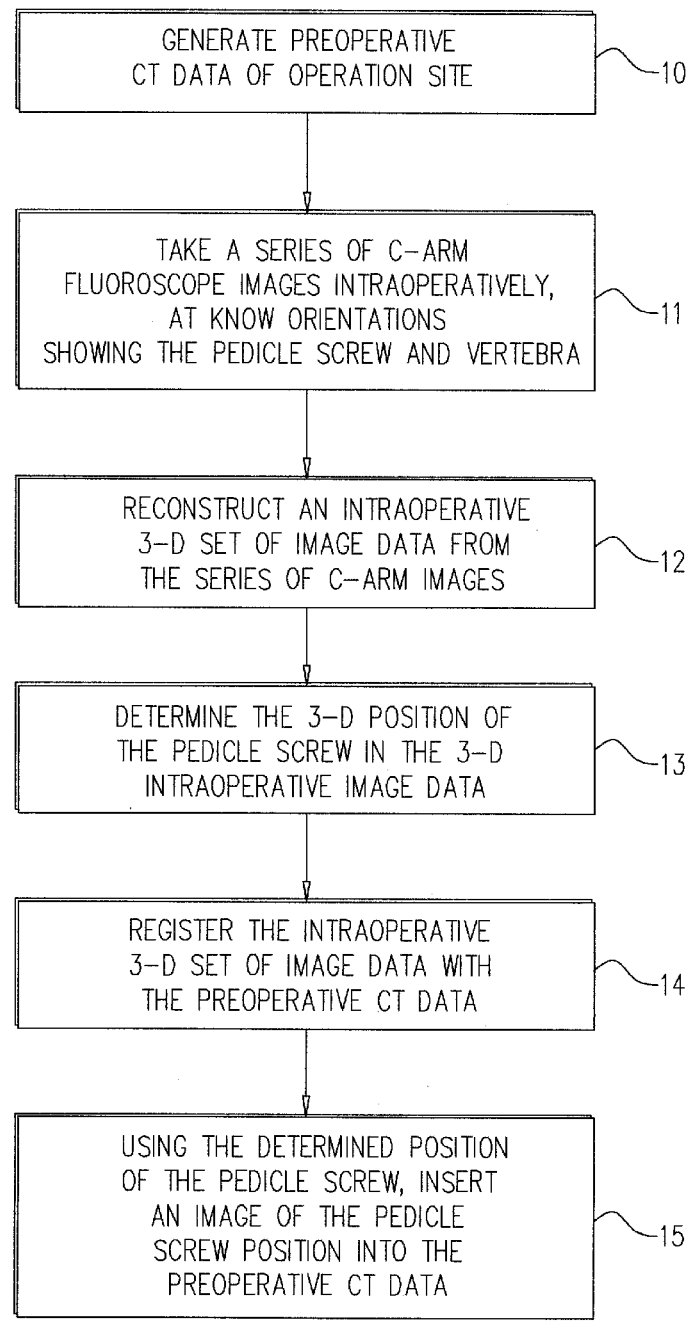
FIG. 1 shows a flow chart describing an exemplary method of the present application, by which the position of a vertebral pedicle screw can be accurately determined intraoperatively.

Reference is now made to FIG. 1, which illustrates schematically a flow chart describing an exemplary method of the present application, by which the position of a vertebral pedicle screw can be accurately determined intraoperatively from a number of two-dimensional C-arm images taken in the operating room. Although the procedure is described in terms of imaging using a C-arm, this is understood to be only one method by which it is possible to obtain a series of two-dimensional intraoperative images at known orientations, and the disclosure is not intended to be limited to use of the C-arm method.

In step 10, a preoperative CT set of images of the operation site is generated and stored in the control system memory. The surgeon may then plan the intended position of the pedicle screw insert on this set of three dimensional preoperative images.

In step 11, a series of C-arm fluoroscope images are taken intraoperatively at known orientations of the C-arm, the images showing the pedicle screw and the vertebra into which pedicle screw has been inserted. If the three dimensional target method is to be used for determining orientation of the images, then the images should also show sufficient of the target to enable an accurate pose of the image to be calculated.

In step 12, the series of C-arm images are processed within the control system in order to reconstruct an intraoperative three-dimensional set of image data.

In step 13, the three dimensional position of the pedicle screw in this reconstructed intraoperative three-dimensional set of image data is calculated.

In step 14, the intraoperative three-dimensional set of image data is registered with the preoperative CT set of images, using image comparison techniques.

In step 15, the calculated position of the pedicle screw obtained in step 13, is inserted into the intraoperative three-dimensional set of image data as reconstructed in step 12.

Figure 2:
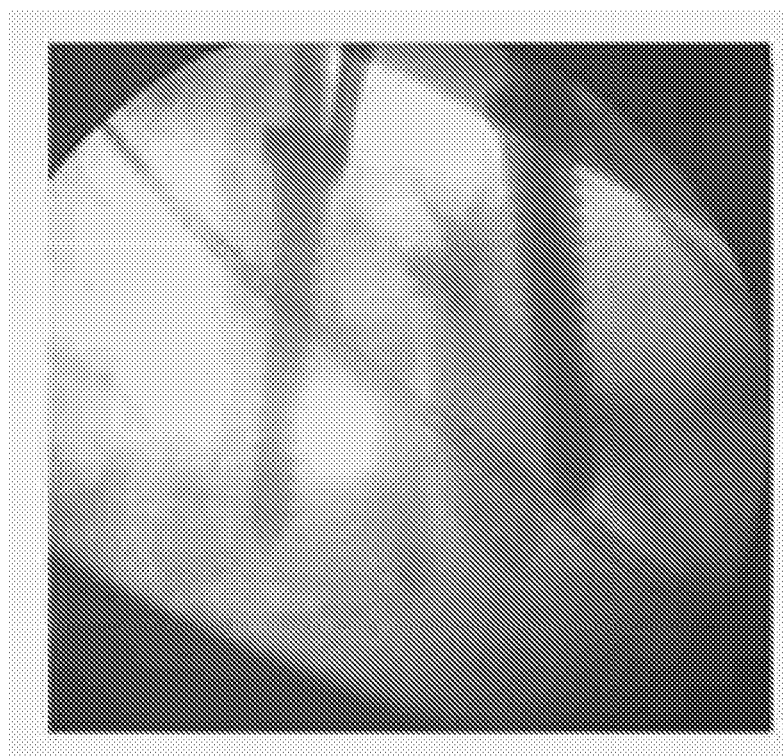
FIG. 2 illustrates a typical LT spinal fluoroscope image with pedicle screws inserted into adjacent vertebrae.

Reference is now made to FIG. 2 which illustrates a typical fluoroscope lateral image taken of the spinal region, showing a pair of adjacent vertebrae with pedicle screws inserted. Although the pedicle screws show up clearly in the image, it is difficult to define the exact position of the screw relative to the vertebra because of the lack of conciseness in the resolution of the details of the parts of the image other than the screw itself, namely the bones and the surrounding tissue. Furthermore, this difficulty is amplified by the essential inability of providing a true axial plane image of the vertebral features, which is generally necessary to accurately determine the position of the pedicle screw. These issues well illustrate the need for a better method of verifying the position of the inserted pedicle screw.

Figure 3:
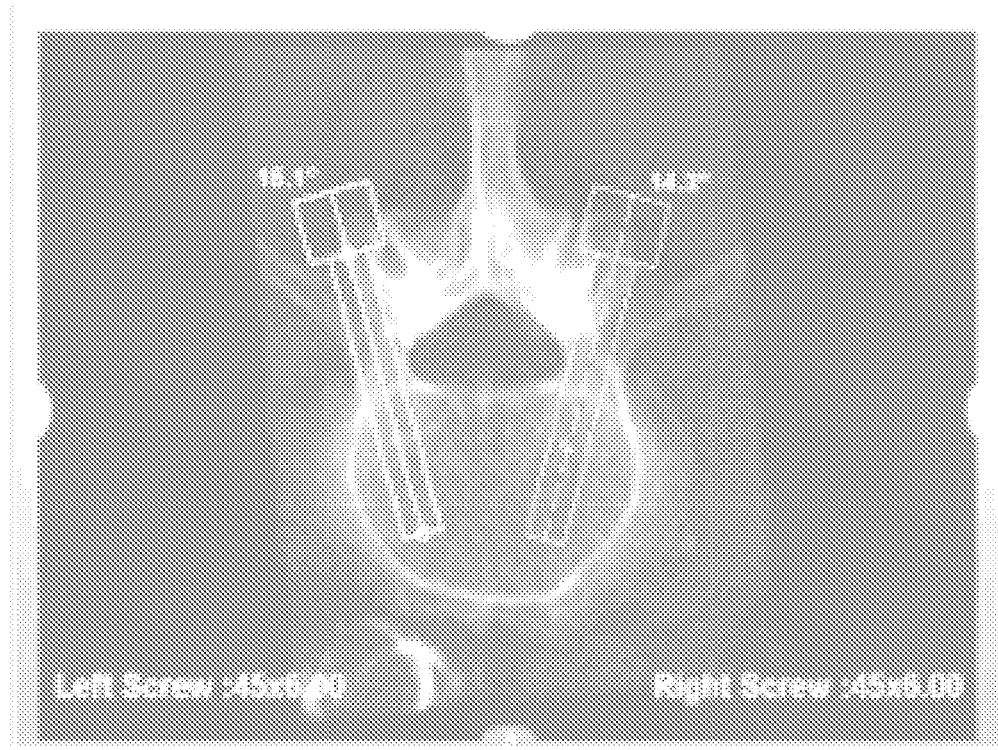
FIG. 3 illustrates a typical axial CT image of a vertebra, showing the preoperatively planned position of the implantation of a pair of pedicle screws.

Reference is now made to FIG. 3 which illustrates a typical axial preoperative CT image of a vertebra, showing the how the surgeon preoperatively plans the position for the implantation of a pair of pedicle screws, carefully aligning them on the preoperative CT images to avoid any neurological damage.

Figure 4A:
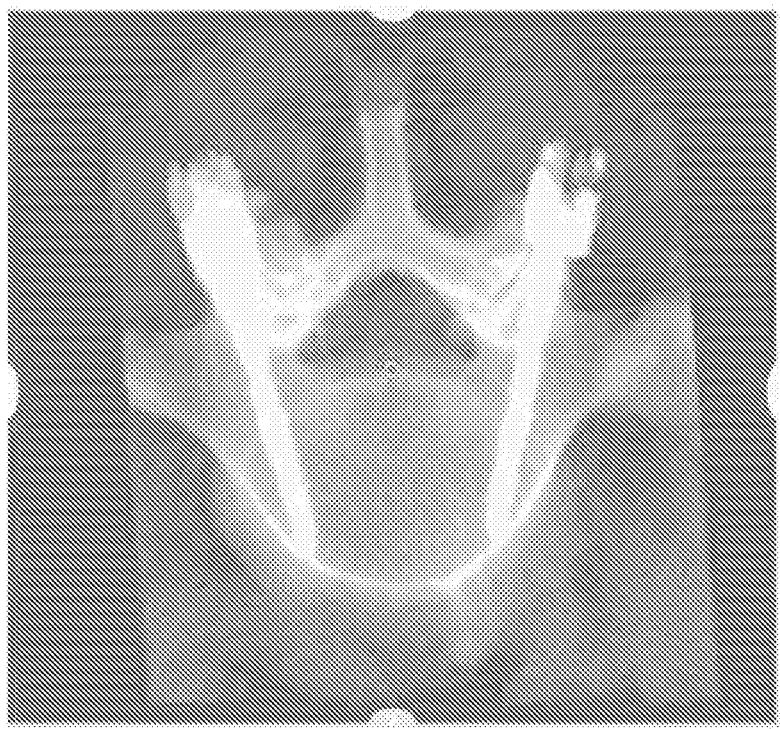
FIGS. 4A and 4B illustrate typical axial CT images of a vertebra, showing the implantation of a pair of pedicle screws whose three dimensional position and orientation relative to the CT image have been obtained using the method shown in the flowchart of FIG. 1.
Figure 4B:
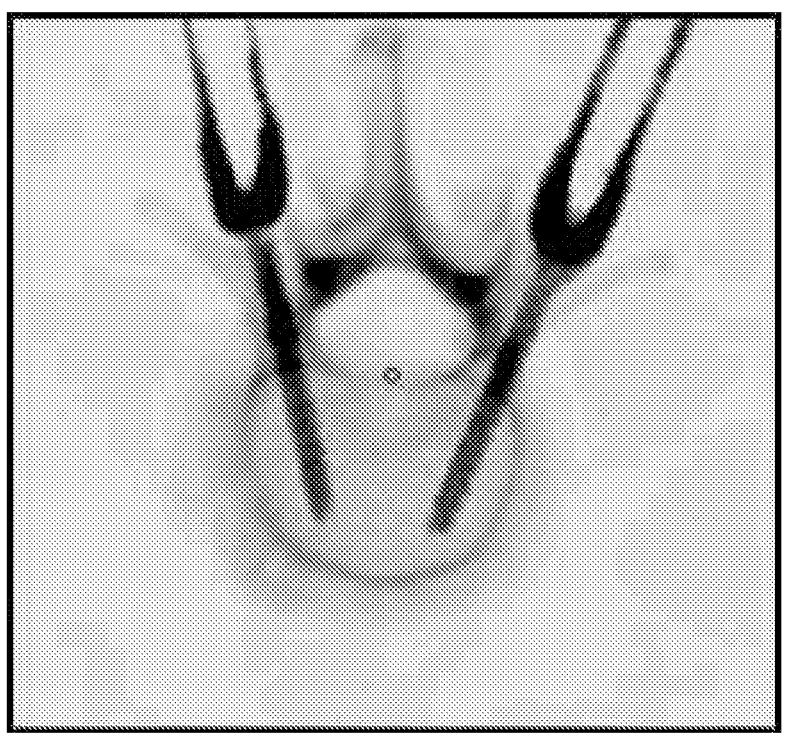

Reference is now made to FIGS. 4A and 4B, which illustrate typical axial preoperative CT images of a vertebra, showing the implantation of a pair of pedicle screws whose position and orientation relative to the CT image have been obtained using the method shown in the flowchart of FIG. 1. FIGS. 4A and 4B show clearly how, using the methods of the present disclosure, both the pedicle screws and the vertebrae features are well defined within such a CT image. FIG. 4A is a negative image, and although not of the same vertebra as the example shown in FIG. 3 (which shows the preplanned position of pedicle screws in a similar vertebra), the ease with which the positional information can be compared with a preplanned position is clear. FIG. 4B is a positive image, which shows clearly the details obtainable by the methods of this application, when compared with the previously obtained type of intraoperative fluoroscope image shown in FIG. 2. FIG. 4B also shows the screwing tool elements attached to the tulip on the heads of the pedicle screws, illustrating how the method can be performed to ascertain the screw position even in mid-operation, when the screws can still be withdrawn in real time.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

The invention claimed is:

1. A method of intraoperatively verifying the position and orientation of an intraoperatively inserted orthopedic insert, comprising:
    generating a preoperative three dimensional image data set showing at least a bone in which said insert is to be inserted;
    generating a plurality of intraoperative two-dimensional fluoroscope images showing said insert and said bone, each image taken at a known orientation and position relative to said bone;
    reconstructing from said plurality of intraoperative two-dimensional fluoroscope images, an intraoperative three dimensional image data set including the three dimensional position and orientation of said insert;
    registering said intraoperative three dimensional image data set with said preoperative three dimensional image data set;
    using said previously determined registration to modify said preoperative three dimensional image data set by insertion therein of the three dimensional position and orientation of said insert; and
    generating at least one two dimensional image from said modified preoperative three dimensional image data set, with a virtual image of said intraoperatively inserted orthopedic insert implanted therein,
    such that the position and orientation of said intraoperatively inserted orthopedic insert may be verified intraoperatively on an image having the characteristics of a preoperatively generated image.

2. A method according to claim 1, further comprising:
    defining on said preoperative three dimensional image data set the planned position and orientation of said insert relative to said bone; and
    comparing said implanted virtual image of said insert in said preoperative three dimensional image data set with said planned position and orientation of said insert relative to said bone.

3. A method according to claim 1, wherein said registering is performed by comparing anatomical features determined from said at least one intraoperative three dimensional image data set with corresponding features on said preoperative three dimensional image data set.

4. A method according to claim 1, wherein said registering is performed by comparing intensity features determined from said at least one intraoperative three dimensional image data set with corresponding features on said preoperative three dimensional image data set.

5. A method according to claim 1, wherein said at least one bone is a vertebra, and said insert is a pedicle screw, an obliquely inserted screw, or an artificial disc.

6. A method according to claim 1, wherein said preoperative three dimensional image data set is either a CT data set or an MRI data set.

7. A method according to claim 1, wherein said plurality of intraoperative two-dimensional fluoroscope images taken at known orientations and positions is obtained using a C-arm system.

8. A method according to claim 1, wherein said known orientations and positions of said plurality of intraoperative two-dimensional fluoroscope images are determined by analyzing images of a three dimensional target disposed in a fixed position relative to said bone, and featured in said plurality of intraoperative two-dimensional fluoroscope images.

9. A method according to claim 8, wherein said three dimensional target comprises radiographically opaque markers having predetermined mutual positions.

10. A method according to claim 1, wherein said known orientations and positions of said plurality of intraoperative two-dimensional fluoroscope images are determined by use of an optical system tracking the orientation and position of the system generating said fluoroscope images.

11. A method according to claim 1, wherein said known orientations and positions of said plurality of intraoperative two-dimensional fluoroscope images are determined by use of orientation sensors on the system generating said fluoroscope images.

12. A method according to claim 1, wherein said plurality of intraoperative two-dimensional fluoroscope images is a video sequence of images.

13. A method according to claim 1, wherein the intraoperative position and orientation of said insert, as determined in said plurality of intraoperative images, is virtually displayed in said three dimensional image data set obtained preoperatively without said insert.

14. A method according to claim 1, wherein said plurality of intraoperative two-dimensional fluoroscope images, each taken at a known orientation and position relative to said bone, shows said insert during insertion into said bone or on completion of insertion into said bone.

\* \* \* \* \*